United States Patent [19]

Moll et al.

[11] Patent Number: 5,030,651

[45] Date of Patent: Jul. 9, 1991

[54] METHODS AND COMPOSITIONS FOR CONTROLLING, PREVENTING AND TREATING OXIDATIVE INSULT IN THE EYE WITH TRANSITION METAL COMPLEXES

[75] Inventors: Hans R. Moll, Weatherford; Mark T. DuPriest, Fort Worth, both of Tex.

[73] Assignee: Alcon Laboratories. Inc., Fort Worth, Tex.

[21] Appl. No.: 355,712

[22] Filed: May 22, 1989

[51] Int. Cl.$^5$ .................. A61K 31/295; A61K 55/02; A61K 31/30; A61K 31/28

[52] U.S. Cl. .................................... 514/502; 514/114; 514/492; 514/499; 514/501; 514/505; 514/912

[58] Field of Search .............. 514/492, 499, 912, 501, 514/502, 505, 114

Primary Examiner—Frederick E. Waddell
Assistant Examiner—Zohreh A. Fay
Attorney, Agent, or Firm—James A. Arno; Sally S. Yeager

[57] ABSTRACT

Methods for preventing and treating oxidative insult to the eye by the administration of transition metal complexes are disclosed.

12 Claims, No Drawings

METHODS AND COMPOSITIONS FOR CONTROLLING, PREVENTING AND TREATING OXIDATIVE INSULT IN THE EYE WITH TRANSITION METAL COMPLEXES

The present invention is directed to metal complexes which are useful in preventing and treating oxidative insult.

According to the present invention, it has been found that metal complexes, particularly transition metal complexes of the following general structure ("TMC") are useful in preventing and controlling oxidative insult, particularly in the eye.

$$L_p M_m \quad [A]$$

wherin L is an organic ligand, M is a transition metal ion and p and m are integers reflecting the nature of the complex, i.e., the ratio of L to M. Examples of preferred TMC are represented by the following structure:

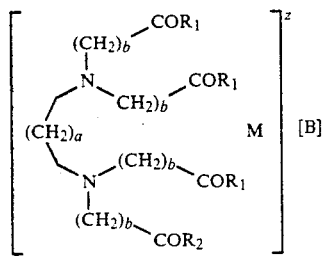

[B]

wherein:
a is 0 or 11
b is 1 or 2;
m is $Fe^{+3}$, $Fe^{+2}$, $Co^{+3}$, $Cr^{+3}$, $V^{+3}$, $Cu^{+2}$ or $Mn^{+2}$;
$R_1=R_2=$—OH or —O—; or
$R_1=$—OH or —O— and $R_2=$—O—alkyl ($C_1$ through $C_{18}$), —O—aryl, —O—alkyl-aryl, —NH—$(CH_2)_n$-NH-peptide (or protein) wherein n=1-6, or —$NR_3R_4$, wherein $R_3$ and/or $R_4$ can be hydrogen, any saturated or unsaturated alkyl or cycloalkyl group ($C_1$ through $C_{18}$), any aryl, alkylaryl, heteroalkyl and heteroaryl group with or without one or more functional groups such as F, Cl, Br or I; amino, imino or nitrilo; alcohol, ether, carbonyl or carboxyl including esters and amides; thiol, thioether, sulfoxide or sulfone; thiocarboxyl and sulfonate including esters and amides; and any phosphorous containing functional group. In addition one or more of any H-atom present in the four acid-moieties and/or in the diamine moieties may be substituted by one or more of the following groups: straight chain and/or branched saturated and unsaturated alKyl groups up to 14 carbons; single and/or polynuclear aryl groups up to 14 carbons; alkyl-aryl groups up to 14 carbons; or saturated and/or unsaturated mono or polynuclear heterocyclic groups. Substitution can result in annelation, giving rise to cyclic and polycyclic molecules. These groups which can be substituted for one or more H atoms and which can give rise to cyclic and polycyclic molecules can contain one or more of the following functional groups, in particular: halogen, such as F, Cl Br or I; amino, imino or nitrilo functions; alcohol, ether, carbonyl and carboxyl functions, including esters and amides; thiol, thio ether, sulfoxide; sulfone, thiocarboxylic and sulfonic acid functions; and phosphorus containing functions.

z is $-1$ when $R_1=R_2=$—$O^-$ or OH and M is $Fe^{+3}$, $Co^{+3}$ or $V^{+3}$; z is $-2$ when $R_1=R_2=$—$O^-$ or —OH and M is $Fe^{+2}$, $Cu^{+2}$ or $Mn^{+2}$. z is 0 when $R_1$ is —$O^-$ or —OH, $R_2$ is an ester or an amide and M is $Fe^{+3}$, $Co^{+3}$, $Cr^{+3}$ or $V^{+3}$.

The most preferred TMC are the iron ($Fe^{+3}$, $Fe^+$) complexes of the organic ligands.

The TMC of the present invention as described above include all sterioisomers of the TMC.

The TMC of the present invention are formed by reacting the organic ligands with metal ions which are capable of complexing substantially simultaneously with both the nitrogen atoms and the carboxylate groups of the organic ligands, resulting in anionic hexadentates or anionic or neutral tetraand pentadentates as shown in [B]. The TMC will be anionic or uncharged depending on the oxidation level of the metal ion and the nature of the ligands. Typically the metal ions will be selected from the group consisting of $Fe^{+3}$, $Co^{+3}$, $Cr^{+3}$, $V^{+3}$, $Cu^{+2}$, and $Mn^{+2}$, preferably $Fe^{+3}$. The synthesis of such TMC is known to those skilled in the art. In general, stoichiometric amounts of the ligand of choice and a water soluble salt of the transition metal such as $FeCl_3$, $Fe(NO)_3$, and $CuCl_2$ are refluxed in water for 5 minutes to an hour. The pH is then adjusted to between 5 and 7 with an appropriate base to provide for the desired salt on crystallization. Most of the water is then evaporated and the TMC is recrystallized from an alcohol, such as methanol, ethanol, propanol, or alcohol/water mixtures. The formation of $Na^+$, $NH_4^+$ and $Ca^{+2}$ salts are described; see, for example, Sawyer et al., *J. Amer. Chem. Soc.*, Vol. 81, 816 (1959); Britzinger et al., *Z. Anorg. Chem.*, Vol. 251, 289 (1943) (ref. Beilstein, Vol. 4, III 1988); and Cohen et al., *J. Amer. Chem. So.*, Vol. 88, 3228 (1966).

Organic ligands which are reacted with metals to form TMC as described above can be made by several methods. In general, this is accomplished by tetraalkylation of the desired diamine with the appropriate acetate or propionate derivative.

The diamino compounds are prepared using standard synthetic methodology familiar to those skilled in the art as described below.

Tetraacetic acid derivatives can be obtained by alkylation of the diamino compound with an excess of an ester of chloro or bromoacetate such as methyl, ethyl, or t-butyl, followed by ester hydrolysis under either acidic (e.g. trifluoroacetic acid or aqueous hydrochloric acid) or basic (e.g. excess sodium or potassium hydroxide or carbonate in aqueous alcohol) conditions. Tetraalkylation can be accomplished in a solvent such as t-butanol in the presence of a base such as sodium or potassium carbonate at 500° C. to reflux for 18 to 48 hours. An alternate method is to use an excess of chloro or bromoacetic acid (for example, see Belcher, R. et. al., *Talanta* 1959, 3, 201).

Tetrapropionic acid derivatives can be obtained by tetraalkylation using acrylonitrile under forcing conditions followed by hydrolysis of the nitrile functionalities to carboxylic acids using concentrated hydrochloric acid or aqueous sulfuric acid. Alternatively, dialkylation to provide N,N'-dipropionic acids is accomplished by alkylation under milder conditions followed by hydrolysis. In this way, N,N'-dipropionic-N,N'-diacetic acids can be obtained by alkylation of the intermediate diacid with an acetic acid derivative as described above.

N,N'-Diacetic acid-N,N'-di-α-substituted acetic acids can be prepared by initial dialkylation of the diamino compound with an α-halo carboxylic acid (other than a haloacetic acid) to obtain an N,N'-di-α-substituted acetic acid followed by dialkylation with chloro or bromoacetic acid or an ester thereof as described above. (For example, see Nakashima, H.; Miyake, M., *Yukagaku* 1972, 21, 416).

N,N,N'-Triacetic acid-N'-acetate compounds can be obtained by incomplete hydrolysis of the tetraesters (for example, see Beilstein, Vol.4, Series III, p.1187).

Monoamide derivatives of ethanediaminetetraacetic acids or propanediaminetetraacetic acids can be prepared by either of two different methods. In the first method, tetraethyl ester derivatives of the diaminetetraacetic acids are hydrolyzed to the triesters using one equivalent of sodium hydroxide in the presence of copper(II) perchlorate. Amide formation is then accomplished with the desired amine and 1,1'-carbonyldiimidazole. The remaining ester functionalities are then hydrolyzed using lithium hydroxide in ethanol (for example, see Hertzberg, R. P.; Dervan, P. B., *Biochemistry* 1984, 23, 3934). The second procedure involves the formation of the cobalt(III) complex of the diaminetetraacetic acid followed by formation of the amide derivative of the uncoordinated carboxylic acid functionality by using the desired amine and 1-ethyl-(3-dimethylaminopropyl) carbodiimide. The cobalt is then removed from the complex by reduction using iron(II) sulfate and ascorbate at pH 5 to provide the desired monoamide ligand (for example, see Haner, M.; Eidson, A. F.; Darnall, D. W.; Birnbaum, E. R., *Arch. Biochem Biophys.* 1984, 231, 477).

Many methods are available for the preparation of substituted ethanediamines and propanediamines. Monosubstituted ethanediamines can be prepared from substituted amino acids by conversion of the carboxylic acid functionality to an amide followed by reduction of the amide to an amine (for example, see Yeh, S. M.; Sherman, D. G.; Meares, C. F., *Anal. Biochem.* 1979, 100, 152). Primary, vicinal diamines can be obtained from a large variety of substituted olefins using several different methods. Olefins can be oxidized to epoxides which are then reacted with azide to provide azide alcohols. Mesylation followed by azide displacement provides a vicinal diazide which can be reduced to the diamine (for example, see Swift, G.; Swern, D., *J. Org. Chem.* 1967, 32, 511). Or olefins can be oxidized to vicinal diols which can be converted to vicinal diamines by the three step sequence consisting of dimesylation, displacement with azide, and azide reduction (for example, see Martin, R. L.; Norcross, B. E., *J. Org. Chem.* 1975, 40, 523 or Feit, P. W.; Nielsen, O. T., *J. Med. Chem.* 1967, 10, 927). Another multistep method is that of Kohn (Kohn, H.; Jung, S-H., *J. Am. Chem. Soc.* 1983, 103, 4106) which consists of reaction of the olefin with cyanamide and N-bromosuccinimide to provide an alkyl cyanamide that is treated with ethanolic hydrogen chloride to effect hydrolysis to an isourea that is cyclized to an imidazoline using triethylamine or sodium bicarbonate which is then hydrolyzed to the diamine using barium hydroxide. Another method is the reaction of olefins with cyclopentadienylnitrosylcobalt dimer in the presence of nitric oxide followed by reduction with lithium aluminum hydride (see Becker, P. N.; Bergman, R. G., *Organomet.* 1983, 2, 787).

1,3-Propanediamines with one or two substituents at the 2 position are available by initial alkylation of malonic acid diesters, reduction of the ester functionalities to alcohols using lithium aluminum hydride, conversion of the alcohols to mesylates, mesylate displacement with either azide or phthalimide, and, with azides, reduction or, with phthalimides, hydrolysis to the diamines. 1,3-Propanediamines substituted at the 1 and/or 3 positions can be obtained from the corresponding 1,3-dicarbonyl compound by conversion to the dioxime followed by reduction to the diamine. This general method is also applicable to 1,2,3-trisubstituted-1,3-propanediamines by starting with the appropriate 2-substituted-1,3-dicarbonyl compound.

Transition metal complexes of the present invention can be made as described herein. The following specific ligands can be reacted with transition metals to form TMC which are useful in preventing oxidative insult to the eye.

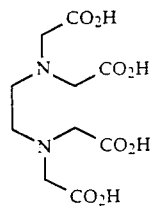

[1]
N,N'-(1,2-Ethanediyl)bis[N-carboxymethyl)glycine]
(available from Sigma Chemical Co. as the iron complex)

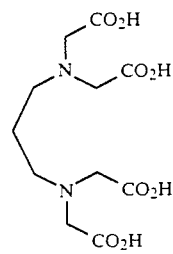

[2]
N,N'-(1,3-Propanediyl)bis[N-carboxymethyl)glycine]

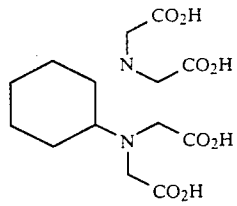

[3]
N,N'-(trans-1,2-Cyclohexanediyl)bis[N-(carboxymethyl)glycine]

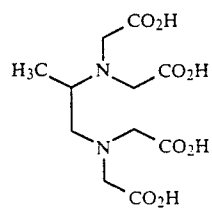

[4]
N,N-(1,2-Propanediyl)bis(N-carboxymethyl)glycine

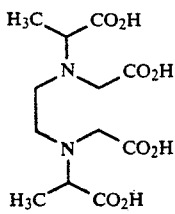

[5]
2,2'-[(1,2-Ethanediyl)bis[(carboxymethyl)imino]]bispropionic acid

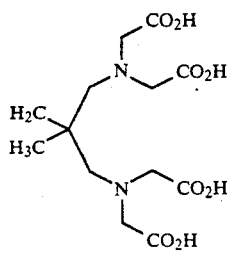

[6]
N,N'-(2,2-Dimethyl-1,3-propanediyl)bis[N-(carboxymethyl)glycine]

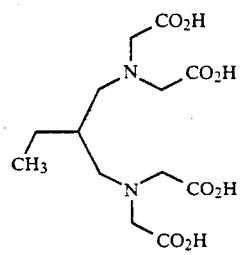

[7]
N,N'-(2-Ethyl-1,3-propanediyl)bis[N-(carboxymethyl)glycine]

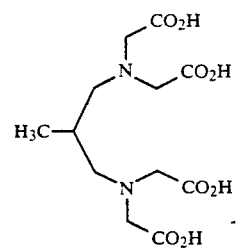

[8]
N,N'-(2-Methyl-1,3-propanediyl)bis[N-(carboxymethyl)glycine]

Chemical species capable of causing oxidative insult can arise in many different ways. As used herein, the term "oxidative insult" refers to the cell death or tissue damage which can result from the presence of oxidizing species as described below. For example, superoxide ($O_2 \cdot ^-$) is produced in vivo by enzymatic, spontaneous and photochemical oxidation reactions; see Fridovich, *The Biology of Oxygen Radicals: General Concepts*. Oxygen Radicals and Tissue Injury, Proceedings of a Brook Lodge Symposium, Augusta, Michigan, April 27-29, 1987. Increased levels of $O_2 \cdot ^-$, which itself is deleterous, can also promote stronger oxidizing species which can cause cell death due to cessation of growth and mutagenesis, Id. Because increased levels of superoxide and other oxidizing agents can lead to severe tissue damage, it is desirable to prevent such oxidative insult by scavenging superoxide and other oxidizing agents. The TMC can, according to the methods disclosed herein, be used in any situation or for any indication in which oxidative insult to the eye may occur. For example, the TMC can be used during and after ophthalmic surgical procedures and for the treatment of inflammation due to allergy, infection, disease or injury, etc.

The transition metal complexes of the present invention may be incorporated in various formulations for delivery to the eye for the prevention and treatment of oxidative insult. For example, topical formulations can be used and can include ophthalmologically acceptable preservatives, surfactants, viscosity enhancers, buffers, sodium chloride and water to form aqueous sterile ophthalmic solutions and suspensions. In order to prepare sterile ophthalmic ointment formulations a transition metal complex is combined with a preservative in an appropriate vehicle, such as mineral oil, liquid lanolin or white petrolatum. Sterile ophthalmic gel formulations comprising TMC can be prepared by suspending the TMC in a hydrophilic base prepared from a combination of, for example, Carbopol-940 (a carboxyvinyl polymer available from B. F. Goodrich Company) according to published formulations for analogous preparations. Preservatives and tonicity agents may also be incorporated in such gel formulations.

The TMC can also be administered systemically, for example, the compounds can be administered orally as incapsulated solids or as aqueous solutions. The compounds can also be administered intravenously or intraperitoneally as aqueous solutions.

The specific types of formulations selected will depend on various factors, such as the TMC being used and the dosage frequency. Topical ophthalmic aqueous solutions, suspensions and gels of TMC of ligands [2], [3], [6], [7] and [8] are preferred dosage forms. Topical formulations of the $Fe^{+3}$ complex of ligand [6] are particularly preferred. The TMC will normally be contained in the formulations at a concentration between about 0.2 to 6.0 weight percent (wt. %), preferably 2.0 to 4.0 wt. %, most preferably about 2.0 wt. %. Thus, for topical administration the formulations are delivered to the surface of the eye one to four times per day, depending on the routine discretion of the skilled clinician.

The following examples are illustrative of complexes and formulations comprising the complexes which can be used according to the present invention for the prevention and treatment of oxidative insult.

EXAMPLE 1

Preparation of N,N'-(1,3-Propanediyl)bis[N-(carboxymethyl) glycine], iron complex, sodium salt The iron complex, sodium salt of ligand [2] was prepared from commercially available propylenediaminetetraacetic acid (Aldrich Chemical Company) using the general method described in Sawyer et al., *J. Amer. Chem. Soc.*, Vol. 82, p.4191 (1960).

EXAMPLE 2

Preparation of N,N'-(trans-1,2-Cyclohexanediyl)bis[N-(carboxymethyl)glycine], iron complex, sodium salt The iron complex, sodium salt of ligand [3] was prepared from commercially available trans-1,2-diaminocyclohexane -N,N,N',N'-tetraacetic acid hydrate (Aldrich Chemical Company as described below.

To a suspension of trans-1,2-diaminocyclohexane -N,N,N',N'-tetraacetic acid hydrate (10 g, 28.9 mmol) in 0.5M aqueous ferric chloride (57.8ml, 1 eq) was added portionwise sodium bicarbonate until the pH was 5.5. The mixture was refluxed for 20 min, cooled, filtered through celite, and evaporated. The residue was taken up in warm (70° C.) dimethylsulfoxide (200mL) and filtered to remove inorganic salts. After the dimethylsulfoxide was removed by evaporation, the residue was recrystallized from water/ethanol to provide 5.5 g (45%) of the complex as green crystals.

Anal. Calcd. for $C_{14}H_{18}N_2O_8FeNa$ $2H_2O$: C, 36.78; ;H, 4.85; N, 6.12. Found: C, 36.27; H, 4.90; N, 612.

EXAMPLE 3

Preparation of N,N'-(1,2-Propanediyl)bis[N-(carboxymethyl) glycine], iron complex, sodium salt The iron complex, sodium salt of ligand [4] was prepared from commercially available 1,2-diaminopropane-N,N,N',N'-tetraacetic acid (Aldrich Chemicl Company) as described below.

1,2-Diaminopropane-N,N,N',N'-tetraacetic acid (10.0 g, 32,6 mmol) was treated with 1 eq of 0.5M aqueous ferric chloride as described in Example 2. Recrystallization from water/ethanol provided 11.2 g (90%) of the complex as a yellow solid.

Anal. Calcd. for $C_{11}H_{14}N_2O_8FeNa$ 1.5 $H_2O$: C, 32.37; H, 4.20; N, 6.86. Found: C, 32.217; H, 4.26; N, 6.78.

EXAMPLE 4

Preparation of 2,2'-[(1,2-Ethanediyl)bis[(carboxymethyl)-iminoII bispropionic acid, iron complex, sodium salt The iron comples, sodium salt of ligand [5] was prepared from commercially available ethylenediamine-N,N'-diacetic acid-N,N'-di-α-propionic acid (Sigma Chemical Company) as described below.

Ethylenediamine-N,N'-diacetic acid-N,N'-di-α-propionic acid (5.0 g, 15.6 mmol) was treated with 1 eq of 0.5M aqueous ferric chlorde as described in Example 2. Recrystallization from water/ethanol provided 1.2 g (19%) of the complex as a bright yellow solid.

Anal. Calcd. for $C_{12}H_{16}N_2O_8FeNa$ 2 $H_2O$: C, 33.43; h, 4.66; N, 6.50. Found: C, 33.58; H, 4.63; N, 6.47.

EXAMPLE 5

The following aqueous formulation can be applied topically to the eye to prevent and treat oxidative insult of the front part of the eye.

| Ingredient | Concentration (w/v %) |
| --- | --- |
| N.N'-(2,2-dimethyl-1,3-propanediyl)bis[N-(carboxymethyl)glycine] iron complex, sodium salt (Ligand 6 Complex) | 2.04 |
| Mannitol | 3.6 |
| Purified water | q.s. to 100 ml |

Procedure

Approximately 85% (8.5 ml) of the batch volume of purified water was added to a container. 204 mg of ligand 6 complex and 360 mg of mannitol were added to the container and mixed well. The pH was adjusted to 6.0. The solution was filtered through a sterilizing filter into a sterile receiving vessel. Purified water (q.s. to 10 ml) was poured through the sterilizing filter and the solution was mixed well.

EXAMPLE 6

The following gel formulation can be prepared and applied topically to the eye to prevent and treat oxidative insult to the front part of the eye.

| Ingredient | Concentration (w/v %) |
| --- | --- |
| N,N'-(2-Ethylpropanediyl)bis[N-(carboxymethyl)glycine] iron complex, sodium salt (Ligand 7 Complex) | 2.0 |
| Carbopol-940 (B. F. Goodrich Company) | 3.0 |
| Mannitol | 3.6 |
| Benzalkonium chloride (BAC) | 0.01 |
| Purified water | q.s. to 100% |

Procedure

Place approximately 85% (8.5 ml) of the batch volume of purified water in a container. Add 0.36 g mannitol, 0.20 Ligand 7 complex, 0.1 ml of 1% BAC and 0.3g carbopol to the water and mix well. Adjust the pH to 6.5 with 0.01N NaOH. Add purified water (q.s. to 10 ml) and mix well to form a gel.

EXAMPLE 7

The following tablet can be administered orally one tablet, 1 to 4 times daily, to prevent and control oxidative insult to the front part of the eye.

| Ingredient | Mg per tablet |
| --- | --- |
| Ligand 6 Complex | 200 mg |
| Starch | 150 mg |

Procedure

Combine Ligand 6 complex (200 mg) and the starch (150 mg) and mix in a P-K twin shell blender (Patterson-Kelly) for 10 minutes. Compress the blended material to form slugs using 1 inch flat face punches. The slugs can then be granulated by passing them through a 16 mesh-screen in a Stokes oscillating granulator (Penwalt Corp., Oak Brook, Ill.). The granulation is then transferred to a Colton rotary tablet press machine hopper (Vector Corp., Marion, Iowa) and compressed into tablets.

We claim:

1. A method for preventing and treating oxidative insult to the eye, which comprises:
    administering a composition comprising a therapeutically effective amount of a transition metal complex comprising an organic ligand which is a non-hetero compound of the following formula and a transition metal ion;

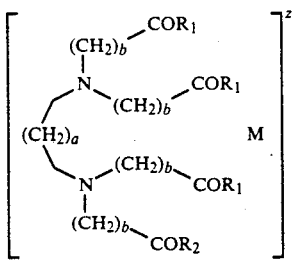

wherein:
a is 0 or 1;
b is 1 or 2;
M is a transition metal ion; and
$R_1 = R_2 = -OH$ or $-O^-$; or
$R_1 = -OH$ or $-O^-$ and $R_2 = -O-$alkyl, ($C_1$ through $C_{18}$), $-O-$aryl, or $-O-$alkyl-aryl, with or without one or more functional groups such as F, Cl, Br or I; amino, imino or nitrilo; alcohol, ether, carbonyl or carboxyl including esters and amides; thiol, thioether, sulfoxide or sulfone; thiocarboxyl and sulfonate including esters and amides; and any phosphorous containing functional group, and one or more of any H-atom present in the four acid-moieties and/or in the diamine moiety may be substituted by one or more of the following groups: straight chain and/or branched saturated and unsaturated alkyl groups up to 14 carbons; single and/or polynuclear aryl groups up to 14 carbons; alkyl-aryl groups up to 14 carbons; and z is $-1$ when $R_1 = R_2 = -O^-$ or OH and M is $Fe^{+3}$, $Co^{+3}$, $Cr^{+3}$ or $V^{+3}$; Z is $-2$ when $R_1 = R_2 = -O^-$ or $-OH$ and M is $Fe^{+2}$, $Cu^{+2}$ or $Mn^{+2}$; z is 0 when $R_1$ is $-O^-$ or $-OH$, $-R_2$ is an ester or amide and M is $Fe^{+3}$, $Co^{+3}$, $Cr^{+3}$ or $V^{+3}$.

2. The method of claim 1 wherein M is $Fe^{+3}$, $Fe^{+2}$, $Co^{+3}$, $Cr^3$, $Cr^3$, $V^{+3}$, $Cu^{+2}$ or $Mn^{+2}$.

3. The method of claim 1 wherein M comprises $Fe^{+3}$.

4. The method of claim 1 wherein the concentration of the compound is between about 0.2–6.0 wt. %.

5. The method of claim 4 wherein the concentration is between about 2.0 and 4.0 wt. %.

6. The method of claim 1 wherein the compound is selected from the group consisting of N,N'-(1,2-ethanediyl) bis[N-(carboxymethyl)glycine], iron complex, sodium salt; N,N'-(1,3-propanediyl)bis-[N-(carboxymethyl)glycine] iron complex, sodium salt; N,N'-(trans-1,2-cyclohexanediyl) bis[N-(carboxymethyl)glycine], iron complex, sodium salt; N,N'-(1,2-propanediyl)bis[N-(carboxymethyl)glycine], iron complex, sodium salt; and 2,2'-[(1,2-ethanediyl)bis[(carboxymethyl) imino]]bispropionic acid, iron complex, sodium salt; N,N'-(2,2-dimethyl-1,3-propanediyl)bis[N-(carboxymethyl)glycine, iron complex, sodium salt; N,N'-(2-ethyl-1,3-propanediyl) bis'N-(carboxymethyl)glycine], iron complex, sodium salt; and N,N'-(2-methyl-1,3-propanediyl)bis[N-(carboxymethyl) glycine], iron complex, sodium salt.

7. The method of claim 6 wherein the compound comprises N,N'-(2,2-Dimethyl-1,3-propanediyl)bis[N-(carboxymethyl)glycine], iron complex, sodium salt.

8. The method of claim 6 wherein the compound concentration is between about 0.2 and 6.0 wt. %.

9. A method for treating oxidative insult to the eye, which comprises:
administering topically to the eye, a therapeutically effective amount of a composition comprising a compound selected from the group consisting of N,N'-(1, 2-ethanediyl)bis[N-(carboxymethyl)glycine], iron complex, sodium salt; N,N'-(1,3-propanediyl)bis-[N-(carboxymethyl)glycine] iron complex, sodium salt; N,N'-(trans-1,2-cyclohexanediyl)bis[N-(carboxymethyl)glycine], iron complex, sodium salt; N,N'-(1, 2-propanediyl)bis[N-(carboxymethyl)glycine], iron complex, sodium salt; 2,2'-[(1,2-ethanediyl)bis[(carboxymethyl)imino]]bispropionic acid, iron complex, sodium salt; N,N'-(2, 2-dimethyl-1,3-propanediyl)bis[N-(carboxymethyl)glycine, iron complex, sodium salt; N,N'-(2-ethyl-1,3-propanediyl)bis'N-(carboxymethyl)glycine], iron complex, sodium salt; and N,N'-(2-methyl-1,3-propanediyl)bis[N-(carboxymethyl)glycine], iron complex, sodium salt.

10. The method of claim 9 wherein the compound comprises N,N'-(1,3-propanediyl)bis-[N-(carboxymethyl)glycine] iron complex, sodium salt; N,N'-(trans-1,2-cyclohexanediyl)bis[N-(carboxymethyl)glycine], iron complex, sodium salt; N,N'-(2, 2-dimethyl-1,3-propanediyl)bis[N-(carboxymethyl)glycine, iron complex, sodium salt; N,N'-(2-ethyl-1,3-propanediyl)bis[N-(carboxymethyl)glycine], iron complex, sodium salt; and N,N'-(2-methyl-1,3-propanediyl)bis[N-(carboxymethyl)glycine], iron complex, sodium salt.

11. The method of claim 9 wherein the concentration is between about 0.2 and 6.0 wt. %.

12. The method of claim 11 wherein the compound concentration is between about 2.0 and 4.0 wt. %.

* * * * *

UNITED STATES PATENT AND TRADEMARK OFFICE
CERTIFICATE OF CORRECTION

PATENT NO. : 5,030,651

DATED : July 9, 1991

INVENTOR(S) : Moll et al.

It is certified that error appears in the above-identified patent and that said Letters Patent is hereby corrected as shown below:

Column 1, line 35, change "a is 0 or 11" to [a is 0 or 1].

Column 2, line 8, change "($Fe^{+3}$; $Fe^{+}$)" to [($Fe^{+3}$, $Fe^{+2}$)].

Column 2, line 55, change "500° C" to [50° C].

UNITED STATES PATENT AND TRADEMARK OFFICE
CERTIFICATE OF CORRECTION

PATENT NO. : 5,030,651                                    Page 2 of 2
DATED      : July 9, 1991
INVENTOR(S): Moll et al.

It is certified that error appears in the above-indentified patent and that said Letters Patent is hereby corrected as shown below:

Column 4, line 45, change

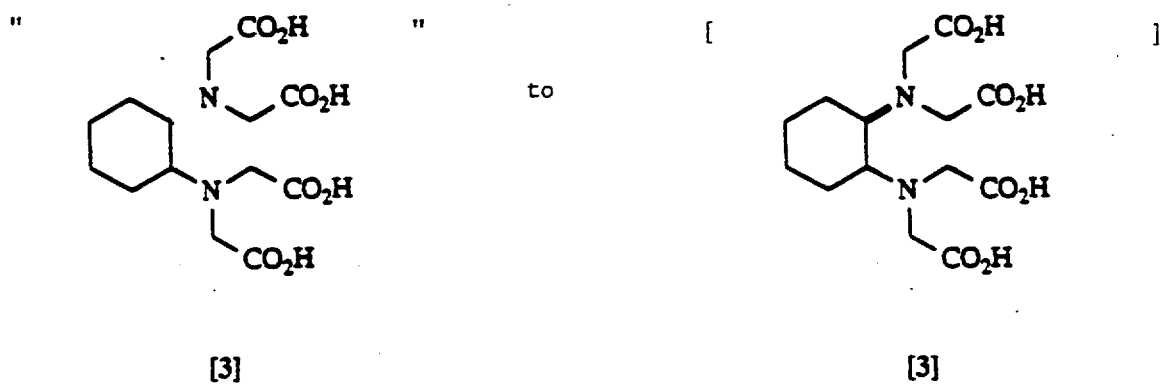

Signed and Sealed this

Tenth Day of January, 1995

*Attest:*

BRUCE LEHMAN

*Attesting Officer*     *Commissioner of Patents and Trademarks*